(12) United States Patent
Grace et al.

(10) Patent No.: US 11,318,253 B2
(45) Date of Patent: May 3, 2022

(54) DART SYRINGE PROJECTILE

(71) Applicant: Clear Dart, L.L.C., Eldon, MO (US)

(72) Inventors: Kevin D. Grace, Eldon, MO (US); Michael A. Graef, Naperville, IL (US)

(73) Assignee: Clear Dart, L.L.C., Eldon, MO (US)

( * ) Notice: Subject to any disclaimer, the term of this patent is extended or adjusted under 35 U.S.C. 154(b) by 918 days.

(21) Appl. No.: 16/116,622

(22) Filed: Aug. 29, 2018

(65) Prior Publication Data

US 2019/0060570 A1   Feb. 28, 2019

Related U.S. Application Data

(60) Provisional application No. 62/551,656, filed on Aug. 29, 2017.

(51) Int. Cl.
| | |
|---|---|
| *A61M 5/20* | (2006.01) |
| *F42B 12/54* | (2006.01) |
| *A61D 7/00* | (2006.01) |
| *F41B 11/85* | (2013.01) |
| *A61D 7/04* | (2006.01) |

(52) U.S. Cl.
CPC ............. *A61M 5/2046* (2013.01); *A61D 7/00* (2013.01); *F42B 12/54* (2013.01); *A61D 7/04* (2013.01); *A61M 2005/2013* (2013.01); *F41B 11/85* (2013.01)

(58) Field of Classification Search
CPC .............. A61M 5/2046; A61M 5/2033; A61M 5/2053; A61M 5/3153; A61M 2005/2013; A42B 12/54; F41B 11/85; A61D 7/04; A61D 7/00
See application file for complete search history.

(56) References Cited

U.S. PATENT DOCUMENTS

| | | | |
|---|---|---|---|
| 3,715,990 A * | 2/1973 | Palmer ................... | F42B 12/54 102/512 |
| 4,717,384 A | 1/1988 | Waldeisen | |
| 5,730,723 A * | 3/1998 | Castellano ............. | A61M 5/30 604/143 |
| 9,234,729 B2 | 1/2016 | Soars | |
| 2015/0352285 A1* | 12/2015 | Soars .................. | A61M 5/2033 604/130 |

* cited by examiner

*Primary Examiner* — Tiffany Legette
(74) *Attorney, Agent, or Firm* — Law Office of Mark Brown, LLC; Mark E. Brown

(57) ABSTRACT

A dart syringe projectile includes a tubular body front and rear ends and a bore extending between said ends. A needle assembly is mounted on the body front end and a tail assembly is mounted on the body rear end. The body bore or the tail assembly receives a striker, a percussion cap positioned in front of the striker, an explosive charge positioned in front of the percussion cap and a plunger positioned in front of the explosive charge. A reservoir cavity in front of the plunger receives a substance for injection. The dart syringe projectile has a flight configuration with the substance in the reservoir cavity and an injection configuration with the plunger propelled forwardly by the explosive charge and the substance discharged from discharge ports in the needle, which are in spaced relation behind a needle tip.

16 Claims, 6 Drawing Sheets

DART SYRINGE PROJECTILE

CROSS REFERENCE TO RELATED APPLICATION

This application claims priority in U.S. Provisional Patent Application No. 62/551,656, filed Aug. 29, 2017, which is incorporated herein by reference.

BACKGROUND OF THE INVENTION

1. Field of the Invention

The present invention relates generally to syringe devices; and in particular to projectile syringes used to inject tranquilizing or medicinal substances into animals.

2. Description of the Related Art

Syringes are often used to administer liquid substances, e.g., tranquilizers and medications, to human and animal subjects. In such fields as veterinary medicine, animal husbandry, livestock handling and wildlife management, domestic and wild animals are treated with various substances for a wide variety of conditions and objectives.

Projectile syringes or darts enable substances to be administered remotely. For example, a veterinarian, or some other individual responsible for administering substances to animals may prefer to maintain a safe distance from the subject animals. Some examples of prior art include Waldeisen U.S. Pat. No. 4,717,384 and Soars U.S. Pat. No. 9,234,729. Those inventions, however, incorporate the use of completely hollow needles that discharge out of the needle tip. This direction of discharge can cause the administered fluid to propel the syringe backward and out of the animal, resulting in incomplete administration. Another weakness of the hollow needle can occur when travel through the air forces air into the dart body, which can dispel a portion of the medication through an increase in air pressure, resulting in a reduction of the intended medication dosage.

Heretofore, there has not been available a dart syringe projectile with the features and advantages of the present invention.

SUMMARY OF THE INVENTION

The invention is a syringe projectile with side discharge needle ports and a firing actuator.

BRIEF DESCRIPTION OF THE DRAWINGS

The drawings constitute a part of this specification and include exemplary embodiments of the present invention illustrating various objects and features thereof.

DETAILED DESCRIPTION OF THE PREFERRED EMBODIMENTS

I. Introduction and Environment

Figure 1:
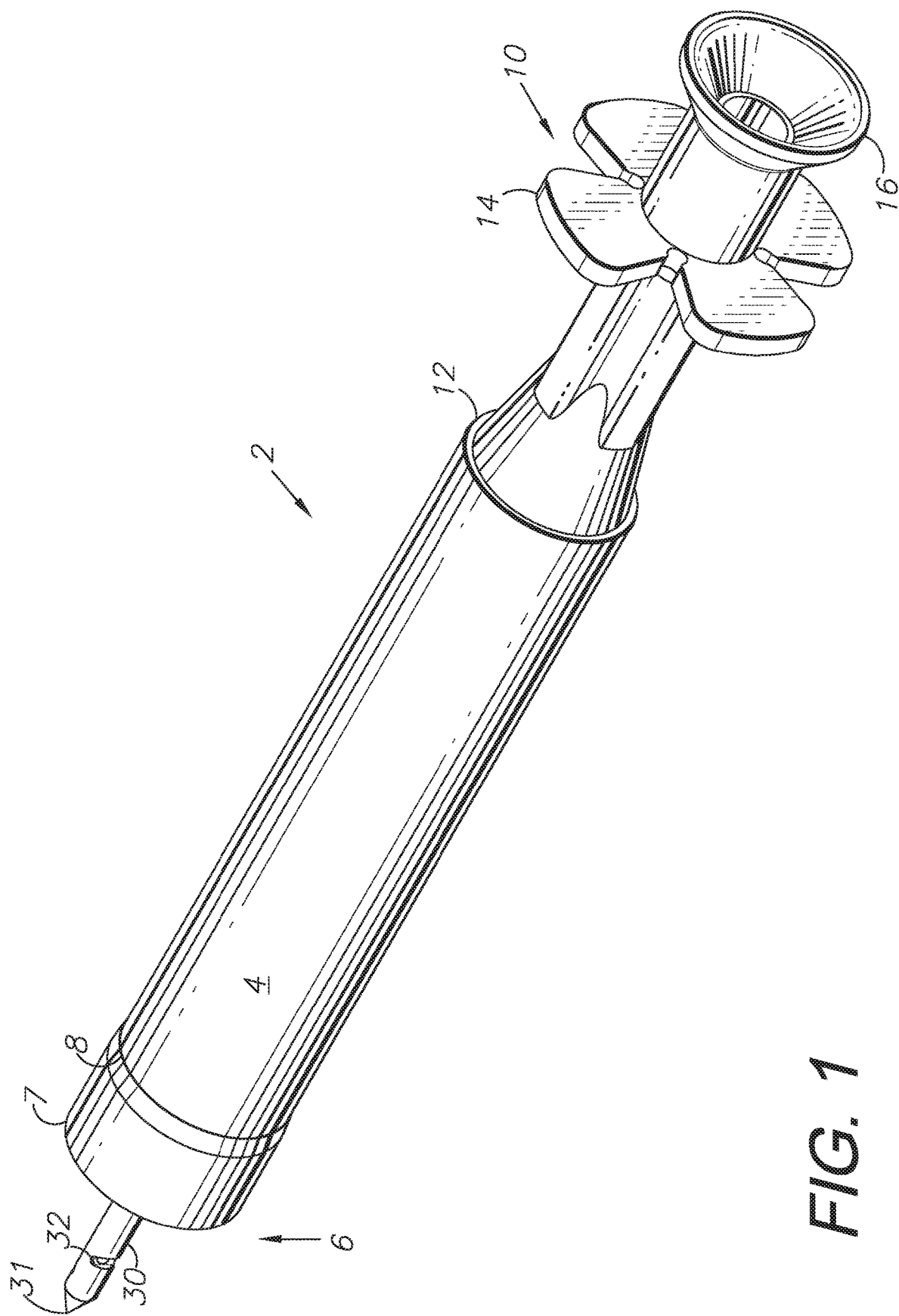
FIG. 1 is a rear perspective view of a dart syringe projectile embodying an aspect of the present invention.
Figure 2:
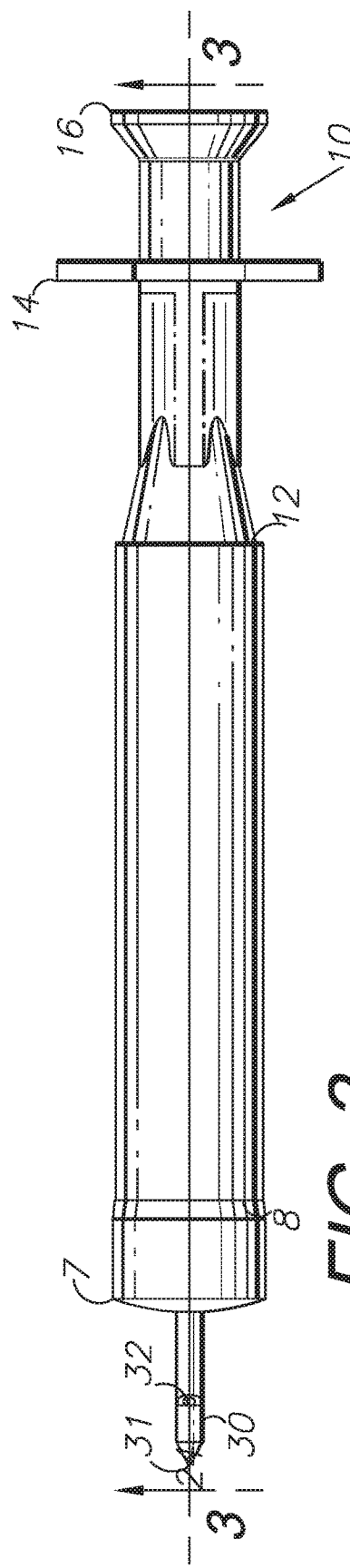
FIG. 2 is a side elevational view thereof.
Figure 3:
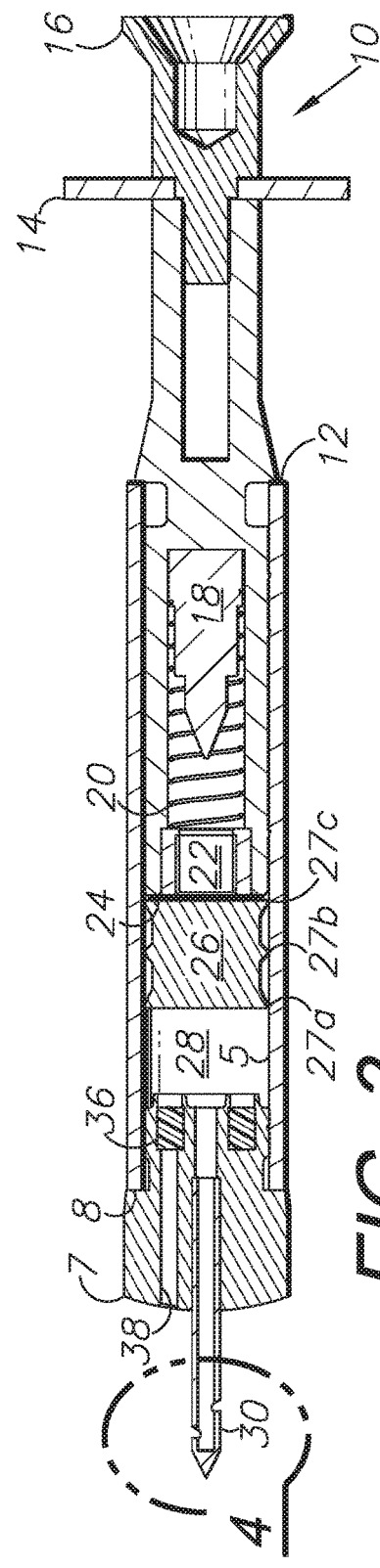
FIG. 3 is a longitudinal, cross-sectional view thereof, taken generally along line 3-3 in FIG. 2.
Figure 4:
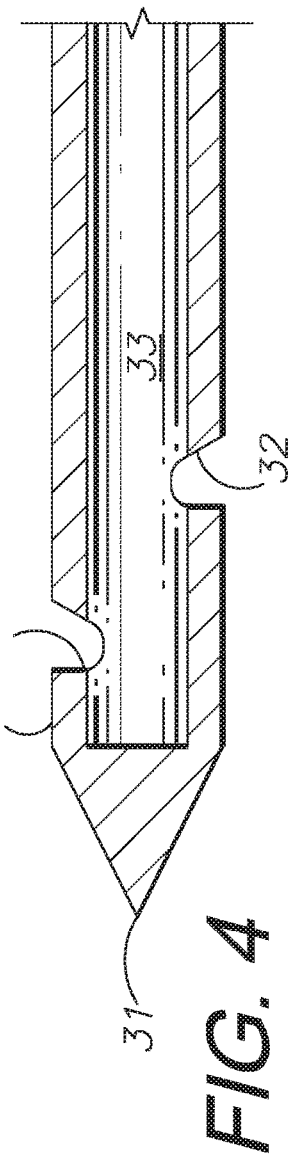
FIG. 4 is an enlarged, fragmentary, cross-sectional view thereof, taken generally in circle 4 in FIG. 3, and particularly showing the needle tip.
Figure 5:
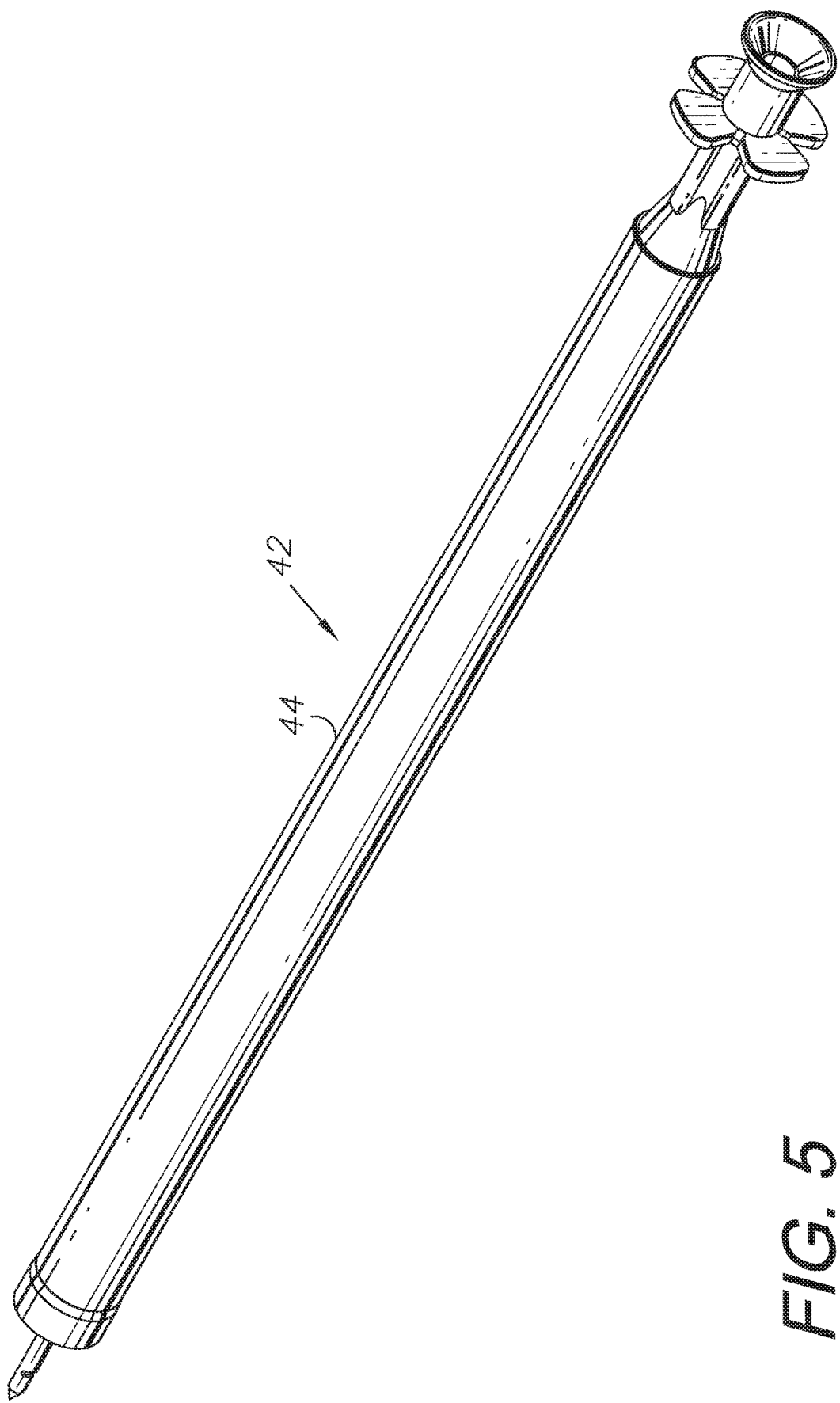
FIG. 5 shows an alternative embodiment of the invention in a rear, perspective view.
Figure 6:
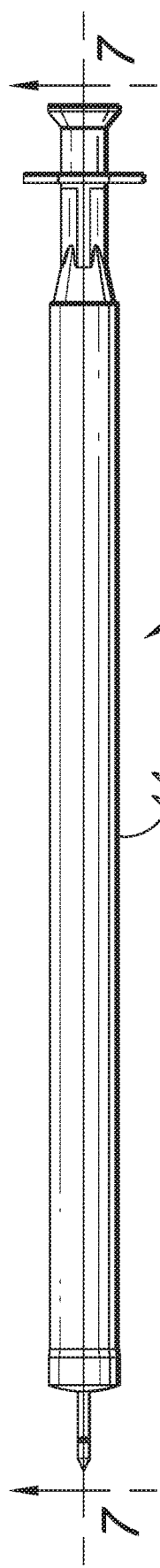
FIG. 6 is a side elevational view thereof.
Figure 7:
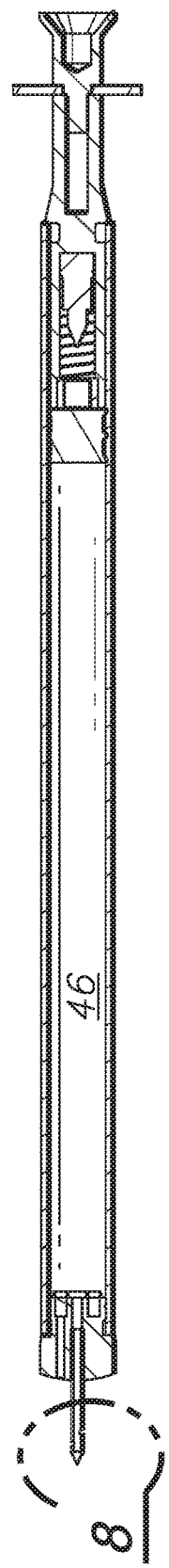
FIG. 7 is a cross-sectional view thereof, taken generally along line 7-7 in FIG. 6.
Figure 8:
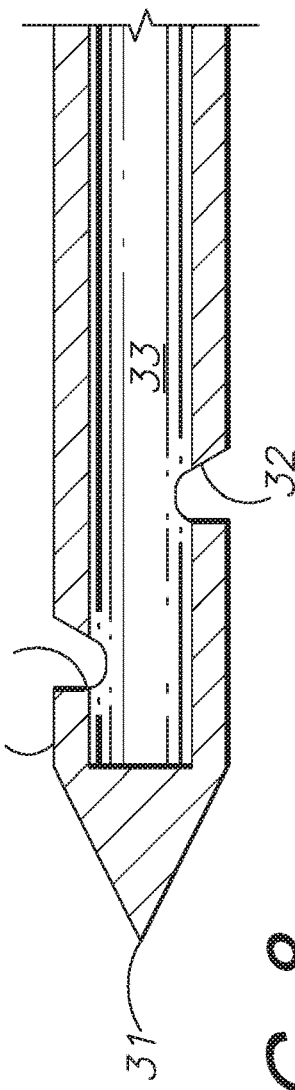
FIG. 8 is an enlarged, fragmentary, cross-sectional view thereof, taken generally in circle 8 in FIG. 7, and particularly showing the needle tip.

As required, detailed aspects of the present invention are disclosed herein, however, it is to be understood that the disclosed aspects are merely exemplary of the invention, which may be embodied in various forms. Therefore, specific structural and functional details disclosed herein are not to be interpreted as limiting, but merely as a basis for the claims and as a representative basis for teaching one skilled in the art how to variously employ the present invention in virtually any appropriately detailed structure.

Certain terminology will be used in the following description for convenience in reference only and will not be limiting. For example, up, down, front, back, right and left refer to the invention as orientated in the view being referred to. The words, "inwardly" and "outwardly" refer to directions toward and away from, respectively, the geometric center of the aspect being described and designated parts thereof. Forwardly and rearwardly are generally in reference to the direction of travel. Said terminology will include the words specifically mentioned, derivatives thereof and words of similar meaning.

II. First Embodiment Dart Syringe Projectile 2 (FIGS. 1-4)

A dart syringe projectile 2 embodying an aspect of the present invention includes a generally tubular body 4 mounting a needle assembly 6 at a body front end 8 and a tail assembly 10 at a body back end 12. The needle assembly 6 includes a needle hub 7 mounting a needle 30 projecting forwardly from the hub 7 to a needle tip 31. A needle cannula 33 opens to side discharge ports 32 positioned in spaced relation behind the needle tip 31. An annular septum ring 36 is embedded in the plunger 26 and is retained therein by heat-welding connecting ears, thus securing the septum ring 36 to the plunger 26. A substance loading passage 38 extends from a front end of the needle hub 7 to the septum ring 36 and receives a hypodermic needle of a syringe with a substance, which can be injected into the reservoir cavity 28 via the septum ring 36. The septum ring 36 preferably comprises a soft, self-sealing rubber material to facilitate loading the reservoir cavity 28 with the substance. The tail assembly 10 can include radially projecting fins 14 and a generally conical, rearmost base 16.

Within the body 4 a striker 18 is biased rearwardly by a spring 20. The striker 18 plunges forwardly against the spring 20 and strikes a percussion cap 22, which ignites a gunpowder charge 24 for propelling a plunger 26 forward to discharge the substance contents from the reservoir cavity 28 via discharge ports 32 in the needle 6 when the projectile strikes a subject, such as an animal. The substance is preferably in liquid form and can comprise a medication, a tranquilizer, a vaccine or any other type of substance intended for direct injection into the subject.

The plunger 26 includes annular front, middle and rear flanges 27a, 27b and 27c, which form sealing connections with a body bore 5 whereby the explosive force from the gunpowder charge 24 is effectively expended propelling the plunger 26 forwardly through the reservoir cavity 28. Moreover, the triple-barrier construction with the flanges 27a, 27b and 27c eliminates or at least minimizes gunpowder residue mixing with substances in the reservoir cavity 28.

In operation, the projectile 2 is preferably loaded into a pneumatic gun, which enables an operator, such as a veterinarian or a livestock handler, to administer a substance from a safe distance. For example, the subject animal can be contained in an enclosure, or unconstrained. When the projectile 2 engages the animal, the needle 6 embeds itself in the flesh, the striker 18 continues traveling forwardly under momentum, striking the percussion cap 22, which discharges the gunpowder charge 24, propelling the plunger 26 through the reservoir cavity 28 whereby the contents thereof are injected via the needle ports 30.

III. Second Embodiment Dart Syringe Projectile 42 (FIGS. 5-8)

FIGS. 5-8 show a second alternative embodiment or aspect dart syringe projectile 42. The projectile 42 includes an elongated body 44 with a correspondingly elongated reservoir cavity 46 for containing a substance.

IV. Third Embodiment Dart Syringe Projectile 52 (FIGS. 9-11)

Figure 9:
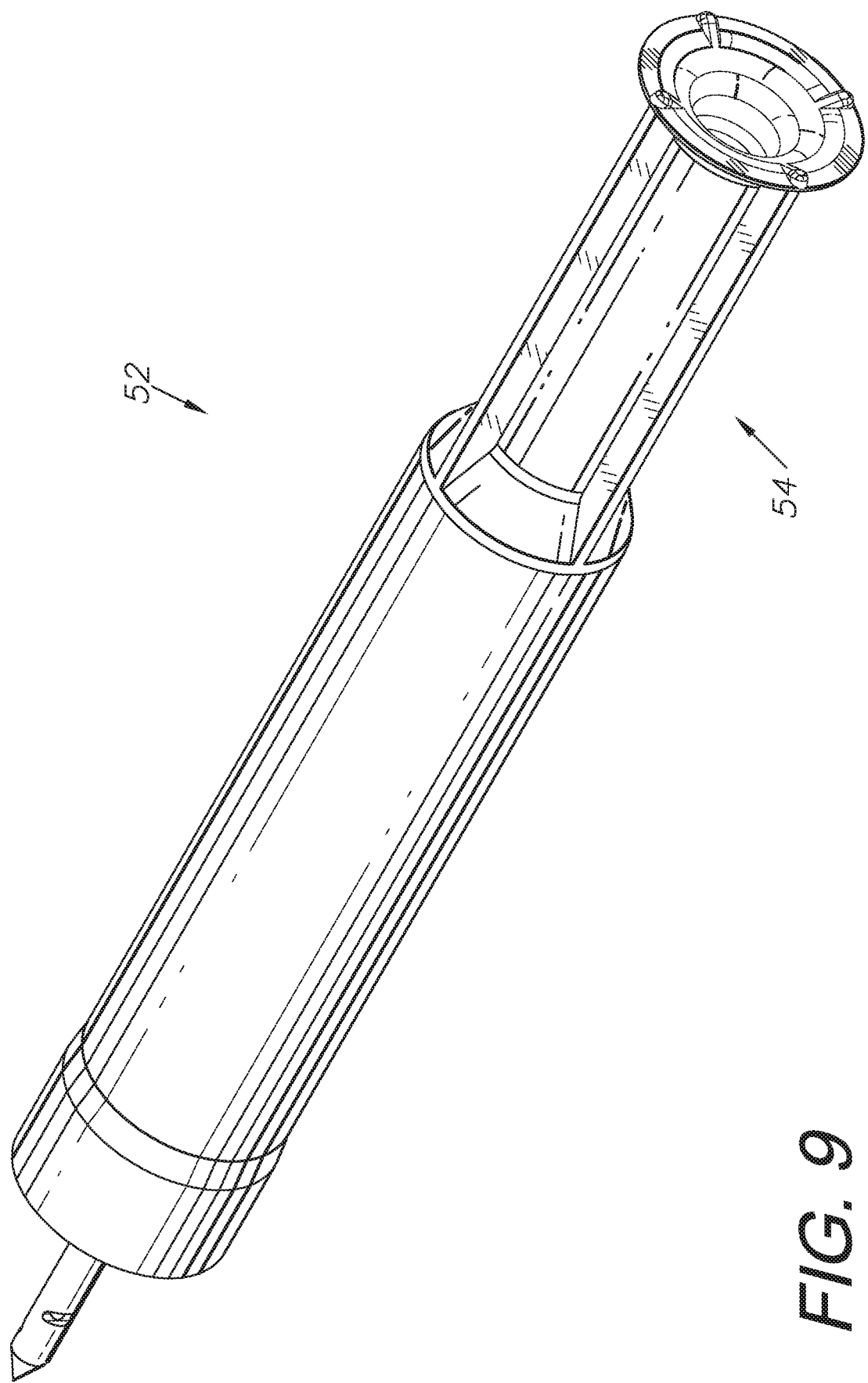
FIG. 9 shows another alternative embodiment of the invention in a rear, perspective view.
Figure 10:
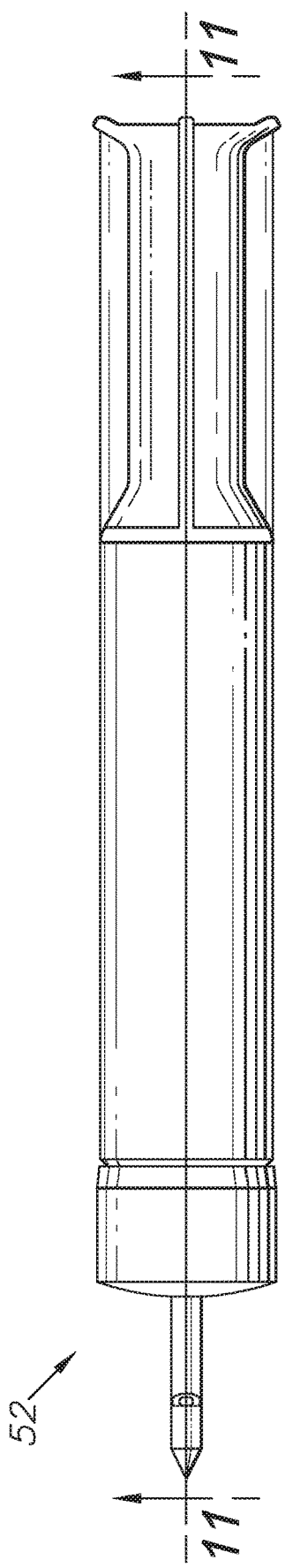
FIG. 10 is a side elevational view thereof.
Figure 11:
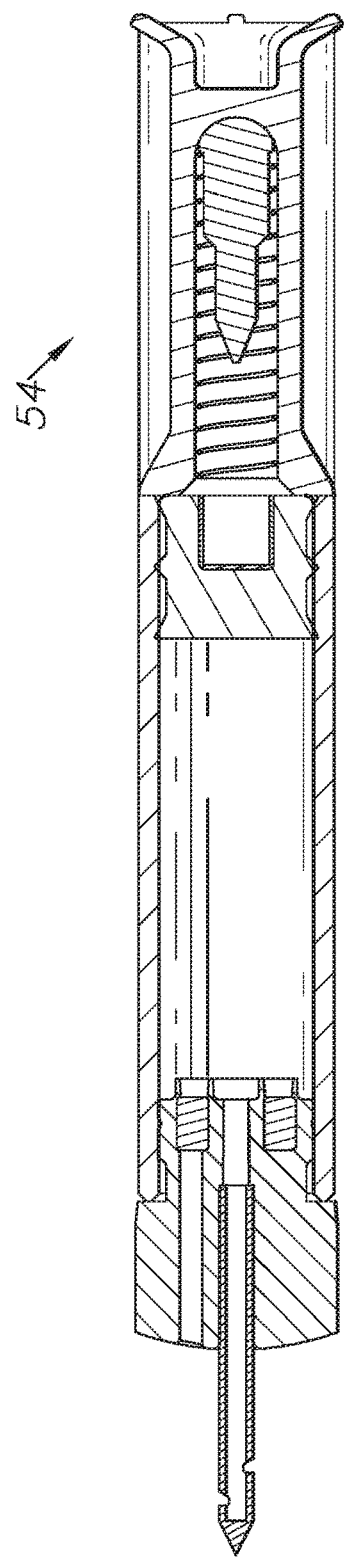
FIG. 11 is a longitudinal, cross-sectional view thereof, taken generally along line 11-11 in FIG. 10.

FIGS. 9-11 show a third alternative embodiment or aspect dart syringe projectile 52 with a modified tail assembly 54 accommodating a more compact projectile 52, as compared to the projectiles 2, 42.

V. Conclusion

The projectiles, e.g., 2, 42 and 52, embodying the present invention are scalable. For example, dosages can be controlled by using different sizes of pneumatic darts, essentially to control the volume of the reservoir cavity particular to a dart. The embodiments featured herein represent a smaller and a larger size, but the projectiles can be virtually any size. Moreover, the projectiles are configured for pre-loading with single dosages and can be discarded after a single use. Alternatively, the projectiles can be configured for reloading and reuse.

It is to be understood that while certain embodiments and/or aspects of the invention have been shown and described, the invention is not limited thereto and encompasses various other embodiments and aspects.

The invention claimed is:

1. A dart syringe projectile, which comprises: a tubular body including front and rear ends and a bore extending between said ends; a needle assembly including a needle hub mounted on said body front end and a hollow hypodermic needle with a discharge needle port, said hollow hypodermic needle received in said needle hub and projecting forwardly therefrom; a tail assembly mounted on said body rear end; a striker movably mounted in said body bore or said tail assembly; a percussion cap mounted in front of said striker in said body bore; an explosive charge in said body bore in front of said percussion cap; a plunger reciprocably mounted in said body bore in front of said explosive charge; a reservoir cavity formed in said body bore in front of said plunger and configured for receiving an injectable substance; said body having a substance loading passage for receiving a hypodermic needle of a syringe containing said injectable substance for loading into said reservoir cavity, and said projectile having a flight configuration with said injectable substance in said reservoir cavity and an inject configuration with said plunger propelled forwardly by said charge and said injectable substance discharged through said discharge needle ports.

2. The dart syringe projectile according to claim 1 wherein said discharge needle port is positioned in spaced relation behind the tip of said needle assembly.

3. The dart syringe projectile according to claim 1 wherein said plunger includes an annular, circumferential flange engaging said tubular body within said body bore, said flange configured for sealing said reservoir cavity and said injectable substance therein from explosive charge residue.

4. The dart syringe projectile according to claim 1 wherein said tail assembly includes multiple fins projecting laterally outwardly therefrom.

5. The dart syringe projectile according to claim 1 wherein said hollow hypodermic needle includes a needle tip, a needle cannula and the needle port comprises multiple discharge ports in spaced relation behind said tip and communicating with said cannula.

6. The dart syringe projectile according to claim 1 wherein said injectable substance comprises a liquid medication or tranquilizer.

7. The dart syringe projectile according to claim 1, further includes: a compression spring engaging said plunger and configured for rearwardly biasing; and said compression spring compressing when said dart syringe projectile is in the inject configuration.

8. The dart syringe projectile according to claim 1 wherein said tubular body comprises a transparent, plastic material.

9. The dart syringe projectile according to claim 1, configured for scaling and thereby accommodating different substance dosages.

10. The dart syringe projectile according to claim 1, configured for propelling from an air gun.

11. The dart syringe projectile according to claim 1 wherein said needle assembly further includes: an annular septum ring within said plunger; and said substance loading passage extending from a front end of said plunger to said septum ring.

12. The dart syringe projectile according to claim 11 wherein said septum ring comprises a soft rubber, self-sealing material.

13. A dart syringe projectile, which comprises: a tubular body including front and rear ends and a bore extending between said ends; a needle assembly including a needle hub mounted on said body front end and a hollow hypodermic needle with a needle port, said hollow hypodermic needle received in said needle hub and projecting forwardly therefrom; said needle port being positioned in spaced relation behind a tip of said hollow hypodermic needle; said needle assembly including: an annular septum ring within a plunger; a substance loading passage extending from a front end of said plunger to said septum ring; and said substance loading passage configured for receiving a hypodermic needle of a syringe containing a substance for loading into a reservoir cavity; a tail assembly mounted on said body rear end; a striker movably mounted in said body bore or said tail assembly; a compression spring engaging said plunger and configured for rearwardly biasing; said compression spring compressing when said dart syringe projectile is in an inject configuration; a percussion cap mounted in front of said striker in said body bore; an explosive charge in said body bore in front of said percussion cap; a plunger reciprocably mounted in said body bore in front of said explosive charge; the reservoir cavity formed in said body bore in front of said plunger and configured for receiving an injectable substance; and said dart syringe projectile having a flight configuration with said injectable substance in said reservoir cavity and the inject configuration wherein in said plunger is configured to be propelled forwardly by said explosive charge and said injectable substance discharged through said needle port.

14. The dart syringe projectile according to claim 13 wherein said tubular body comprises a transparent, plastic material.

15. The dart syringe projectile according to claim 13, which is configured for scaling and thereby accommodating different substance dosages.

16. The dart syringe projectile according to claim 13, which is configured for propelling from an air gun.

* * * * *